United States Patent [19]
Bandman et al.

[11] Patent Number: 5,972,684
[45] Date of Patent: Oct. 26, 1999

[54] CARBONIC ANHYDRASE VIII

[75] Inventors: Olga Bandman, Mountain View; Henry Yue, Sunnyvale; Sara R. Greenwald, San Francisco; Neil C. Corley, Mountain View, all of Calif.

[73] Assignee: Incyte Pharmaceuticals, Inc., Palo Alto, Calif.

[21] Appl. No.: 08/977,767

[22] Filed: Nov. 25, 1997

[51] Int. Cl.$^6$ .............................. C12N 9/88; C12N 15/00; C12Q 1/68; C12P 21/06
[52] U.S. Cl. .......................... 435/232; 435/6; 435/320.1; 435/325; 435/69.1; 536/23.2; 536/23.1
[58] Field of Search ................................ 435/232, 320.1, 435/325, 69.1, 6; 536/23.2, 23.1, 23.4, 23.5

[56] References Cited

U.S. PATENT DOCUMENTS 5,589,579  12/1996  Torczynski et al. .................... 536/23.1

OTHER PUBLICATIONS

Adams, M. et al., Genbank Database, Accession No. T34770, Sep. 1995.

Puscas I. et al., "Isosorbide Nitrates, Nitroglycerin, and Sodium Nitroprusside Induce Vasodilation Concomitantly With Inhibition of Carbonic Anhydrase I in Erythrocytes" *Am.J.Hypertens.* (1997) 10:124–128.

Catala, Martin, "Carbonic anhydrase activity during development of the choroid plexus in the human fetus" *Childs Nerv.Syst.* (1997) 13:364–368.

Henry, R.P. et al., "Carbonic anhydrase facilitates $CO_2$ and $NH_3$ transport across the sarcolemma of trout white muscle" *Am.J.Physiol.* (1997) 272:R1754–R1761.

Ridderstrale, Y. et al., "Carbonic Anhydrase Activity in Different Placenta Types: A Comparative Study of Pig, Horse, Cow, Mink, Rat, and Human" *Microsc.Res.Tech.* (1997) 38:115–124.

Bergenhem, N. et al., "Evidence for an initial fast nucleation process in the folding of human carbonic anhydrase I" *Int.J.Pept.Protein Res.* (1989) 33:140–145.

Chakravarty, S. and Kannan, K.K. "Drug–Protein Interactions. Refined Structures of Three Sulfonamide Drug Complexes of Human Carbonic Anhydrase I Enzyme" *J.Mol. Biol.* (1994) 243:298–309.

Briganti, F. et al., "Carbonic Anhydrase Activators: X–ray Crystallographic and Spectroscopic Investigations for the Interaction of Isozymes I and II with Histamine" *Biochemistry* (1997) 36:10384–10392.

Boren, K. et al., "A comparative CD study of carbonic anhydrase isoenzymes with different number of tryptophans: Impact on calculation of secondary structure content" *Protein Sci.* (1996) 5:2479–2484.

Puscas, I. et al., "Nonsteroidal Anti–Inflammatory Drugs Activate Carbonic Anhydrase By a Direct Mechanism of Action" *J.Pharmacol.Exp.Ther.* (1996) 277:1464–1466.

Fauci, A.S. et al., editors, *Harrison's Principles of Internal Medicine* (1994) McGraw–Hill, New York, NY, pp. 776, 777, 855 and 1597.

Parkkila, A.K. et al., "Carbonic anhydrase II in the cerebrospinal fluid: its value as a disease marker" *Eur.J.Clin.Invest.* (1997) 27:392–397.

Gramlich, T.L. et al., "Immunohistochemical Localization of Sodium–Potassium–Stimulated Adenosine Triphosphatase and Carbonic Anhydrase in Human Colon and Colonic Neoplasms" *Arch.Pathol.Lab.Med.* (1990) 114:415–419.

Felix, et al., "Recent developments in the understanding of the pathophysiology of osteopetrosis" *Euro.J.Endocrin.* (1996) 134:143–156.

Centofanti, M. et al., "Comparative Effects on Intraocular Pressure Between Systemic and Topical Carbonic Anhydrase Inhibitors: A Clinical Masked, Cross–Over Study" *Pharmacol.Res.* (1997) 35:481–485.

Suki, W.N., "Use of diuretics in chronic renal failure" *Kidney International* (1997) 51:S–33–S–35.

Cowen, M.A. et al., "A Treatment for Tardive Dyskinesia and Some Other Extrapyramidal Symptoms" *J.Clin.Psychopharm.* (1997) 17:190–193.

Reiss, W.G. and Oles, K.S., "Acetazolamide in the Treatment of Seizures" *Neurology* (1996) 30:514–519.

Yoshida, K., "Effects of Thyroid Hormone on Erythrocyte Carbonic Anhydrase–I and Zinc Concentrations In Vivo and In Vitro: Clinical Usefulness of Carbonic Anhydrase–I and Zinc Concentrations in Erythrocytes" *Tohoku J.Exp.Med.* (1996) 178:345–356.

Kondo, T. et al., "Estimation and characterization of glycosylated carbonic anhydrase I in erythrocytes from patients with diabetes mellitus" *Clin.Chim. Acta* (1987) 166:227–236.

Brinton, D.A., et al., "Endometriosis: Identification by Carbonic Anhydrase Autoantibodies and Clinical Features" *Ann.Clin.Lab.Sci.* (1996) 26:409–420.

D'Cruz, O.J. et al., "Antibodies to carbonic anhydrase in endometriosis: prevalence, specificity, and relationship to clinical and laboratory parameters" *Fertility and Sterility* (1996) 66:547–556.

Lovejoy, D.A., (GI 1532041), GenBank Sequence Detabase (Accession Y07785), National Center for Biotechnology Information, National Library of Medicine, Bethesda, Maryland, 20894. (GI 1932042) (1996).

Swiss–Prot: Accession #P00915, Swiss–Prot Protein Sequence Data Bank, Geneva, Switzerland (1988).

Swiss–Prot: Accession #P00918 Swiss–Prot Protein Sequence Data Bank, Geneva Switzerland (1986).

(List continued on next page.)

*Primary Examiner*—Robert A. Wax
*Assistant Examiner*—Peter P. Tung
*Attorney, Agent, or Firm*—Incyte Pharmaceuticals Inc.

[57] ABSTRACT

The invention provides a human carbonic anhydrase isoform (CAVIII) and polynucleotides which identify and encode CAVIII. The invention also provides expression vectors, host cells, agonists, antibodies and antagonists. The invention also provides methods for treating disorders associated with expression of CAVIII.

10 Claims, 11 Drawing Sheets

OTHER PUBLICATIONS

Swiss–Prot: Accession #P07451, Swiss–Prot Protein Sequence Data Bank, Geneva, Switzerland (1988).

Swiss–Prot: Accession #P22748, Swiss–Prot Protein Sequence Data Bank, Geneva, Switzerland (1992).

Swiss–Prot: Accession #P35218, Swiss–Prot Protein Sequence Data Bank, Geneva, Switzerland (1994).

Swiss–Prot: Accession #P23280, Swiss–Prot Protein Sequence Data Bank, Geneva, Switzerland (1991).

Swiss–Prot: Accession #P43166, Swiss–Prot Protein Sequence Data Bank, Geneva, Switzerland (1995).

Swiss–Prot: Accession #P35219, Swiss–Prot Protein Sequence Data Bank, Geneva, Switzerland (1994).

Shingles, R. and Moroney, J.V., "Measurement of Carbonic Anhydrase Activity Using a Sensitive Fluorometric Assay" *Anal.Biochem.* (1997) 252:190–197.

```
              9      18     27     36     45     54
5' NNC TGG AAA NGA GAN ANG NAG GAN GAG GAG ATG CGG GAT GGA GAC CTG GAG 63     72     81     90     99    108
   TTA GGT GGC TTG GGA GAG CTT AAT GAA AAG AGA ACG GAG AGG TGT GGG TTA 117    126    135    144    153    162
   GGA ACC AAG AGG TAG CCC TGG GGG CAG CAG AAG GCT GAG AGG AGT AGG AAG ATC 171    180    189    198    207    216
   AGG AGC TAG AGG GAG ACT GGA GGG TTC CGG GAA AAG AGC AGA GGA AAG AGG AAA 225    234    243    252    261    270
   GAC ACA GAG AGA CGG GAG AGA GAA GAA GAG TGG GTT TGA AGG GCG GAT CTC AGT 279    288    297    306    315    324
   CCC TGG CTG CTT TGG CAT TTG GGG AAC TGG GAC TCC CTG TGG GGA GGA GAG GAA 333    342    351    360    369    378
   AGC TGG AAG TCC TGG AGG GAC AGG GTC CCA GAA GGG GAC GGA AGA GGA GCT GAG 387    396    405    414    423    432
   AGA GGG GGG CAG GGC GTT GGG CAG GGG TCC CTC CTC GGA GGC CTC CTG GGG ATG GGG
                                                                      M   G
```

FIGURE 1A

```
441 GCT GCA GCT CGT CTG AGC GCC CCT CGA GCG CTG GTA CTC TGG GCT GCA CTG GGG 486
    A   A   A   R   L   S   A   P   R   A   L   V   L   W   A   A   L   G

495 GCA GCA GCT CAC ATC GGA CCA GCA CCT GAC CCC GAG GAC TGG AGC TAC AAG     540
    A   A   A   H   I   G   P   A   P   D   P   E   D   W   S   Y   K

549 GAT AAT CTC CAG GGA AAC TTC GTG CCA GGG CCT CCT TTC TGG GGC CTG GTG AAT 594
    D   N   L   Q   G   N   F   V   P   G   P   P   F   W   G   L   V   N

603 GCA GCG TGG AGT CTG TGT GCT GTG GGG AAG CGG CAG AGC CCC GTG GAT GTG GAG 648
    A   A   W   S   L   C   A   V   G   K   R   Q   S   P   V   D   V   E

657 CTG AAG AGG GTT CTT TAT GAC CCC TTT CTG CCC CCA TTA AGG CTC AGC ACT GGA 702
    L   K   R   V   L   Y   D   P   F   L   P   P   L   R   L   S   T   G

711 GGA GAG AAG CTC CGG GGA ACC TTG TAC AAC ACC GGC CGA CAT GTC TCC TTC CTG 756
    G   E   K   L   R   G   T   L   Y   N   T   G   R   H   V   S   F   L

765 CCT GCA CCC CGA CCT GTG GTC AAT GTG TCT GGA GGT CCC CTC TAC AGC CAC     810
    P   A   P   R   P   V   V   N   V   S   G   G   P   L   Y   S   H
```

```
819                 828                 837                 846                 855                 864
CGA CTC AGT GAA CTG CGG CTG CTG TTT GGA GCT CGC GAC GGA GCC GGC TCG GAA
 R   L   S   E   L   R   L   L   F   G   A   R   D   G   A   G   S   E 873                 882                 891                 900                 909                 918
CAT CAG ATC AAC CAC CAG CAG GGC TTC TCT GCT GAG GTG CAG CTC ATT CAC TTC AAC
 H   Q   I   N   H   Q   Q   G   F   S   A   E   V   Q   L   I   H   F   N 927                 936                 945                 954                 963                 972
CAG GAA CTC TAC GGG AAT TTC AGC ACT GCT GCC TCC CGC CCC GGC CCC AAT GGC CTG GCC
 Q   E   L   Y   G   N   F   S   T   A   A   S   R   P   G   P   N   G   L   A 981                 990                 999                 1008                1017                1026
ATT CTC AGC CTC TTT GTC AAC GTT GCC TCT ACC ATC CGC ATC CTC AGT TTT
 I   L   S   L   F   V   N   V   A   S   T   I   R   I   L   S   F 1035                1044                1053                1062                1071                1080
CTC CTT AAC CGC GAC ACC ATC ACT CGC ATC TCC TAC AAG AAT GAT GCC TAC TTT
 L   L   N   R   D   T   I   T   R   I   S   Y   K   N   D   A   Y   F 1089                1098                1107                1116                1125                1134
CTT CAA GAC CTG AGC CTG GAG CTC CTG TTC CCT GAA TCC TTC GGC TTC ATC ACC
 L   Q   D   L   S   L   E   L   L   F   P   E   S   F   G   F   I   T 1143                1152                1161                1170                1179                1188
TAT CAG GGC TCT CTC AGC ACC CCG CCC TGC TCC GAG ACT GTC ACC TGG ATC CTC
 Y   Q   G   S   L   S   T   P   P   C   S   E   T   V   T   W   I   L
```

```
          1197           1206           1215           1224           1233           1242
ATT GAC CGG GCC CTC AAT ATC ACC TCC CTT CAG ATG CAC TCC CTG AGA CTC CTG
 I   D   R   A   L   N   I   T   S   L   Q   M   H   S   L   R   L   L 1251           1260           1269           1278           1287           1296
AGC CAG AAT CCT CCA TCT CAG ATC TTC CAG AGC CTC AGC GGT AAC AGC CGG CCC
 S   Q   N   P   P   S   Q   I   F   Q   S   L   S   G   N   S   R   P 1305           1314           1323           1332           1341           1350
CTG CAG CCC TTG GCC CAC AGG GCA CTG AGG GGC AAC AGG GAC CCC CGG CAC CCC
 L   Q   P   L   A   H   R   A   L   R   G   N   R   D   P   R   H   P 1359           1368           1377           1386           1395           1404
GAG AGG CGC TGC CGA GGC CCC AAC TAC CGC CTG CAT GTG GAT GGT GTC CCC CAT
 E   R   R   C   R   G   P   N   Y   R   L   H   V   D   G   V   P   H 1413           1422           1431           1440           1449           1458
GGT CGC TGA GAC TCC CCT TCG AGG ATT GCA CCC GCC CGT CCT AAG CCT CCC CAC
 G   R 1467           1476           1485           1494           1503           1512
AAG GCG AGG GGA GTT ACC CCT AAA ACA AAG CTA TTA AAG GGA CAG AAT ACT TCC

| | | | | | | | |
|---|---|---|---|---|---|---|---|
| 111 | PAPRPVVNV- | -SGGPLLYSHRLSELRLLFGARD- | ---- | -GAGSEH | 2059155 |
| 70 | FEDNDRSVLKGGPFSDSYRLFQFHFHWGSTN- | ---- | -EHGSEH | CA1 |
| 69 | FDDSQDKAVLKGGPLDGTYRLIQFHFHWGSLD- | ---- | -GQGSEH | CA2 |
| 69 | FDDTYDRSMLRGGPLPGPYRLRQFHFHWGSSD- | ---- | -DHGSEH | CA3 |
| 94 | LENKASISG-GGLPAPYQAK- | -QLHLHWSDLP- | ---- | -YKGSEH | CA4 |
| 106 | FDDATEASGISGGPLENHYRLKQFHFHWGAVN- | ---- | -EGGSEH | CA5 |
| 91 | LPSTMRMTV- | -AD-GIVYIAQ- | -QMHFHWGASSEISGSEH | CA6 |
| 72 | FNDSDDRTVTGGPLEGPYRLKQFHFHWGKKH- | ---- | -DVGSEH | CA7 |
| 93 | LKKSVLSG- | -GPLPQGHEFELYEVRFHWGREN- | ---- | -QRGSEH | CA? |

| | | | | |
|---|---|---|---|---|
| 148 | QINHQGFSAEVQLIHFNQELYGNFSA- | -ASRGPNGLAILS | 2059155 |
| 108 | TVDGVKKYSAELHVAHWNSAKYSSLAE- | -AASKADGLAVIG | CA1 |
| 107 | TVDKKKYAAELHLVHWN-TKYGDFGK- | -AVQQPDGLAVLG | CA2 |
| 107 | TVDGVKKYAAELHLVHWN-PKYNTEKE- | -AVAGDGIAVIG | CA3 |
| 129 | SLDGEHFAMEMHIHWHEKEK-GTSRNVKE- | -ALKQRDDPEDEIAVLA | CA4 |
| 144 | TVDGHAYPAELHLIVHYNSVKYQNYKE- | -AVVGENGLAVIG | CA5 |
| 127 | TVDGIRHVIELHLIHYNAKKYSK-YKTYDI- | -AQDAPDGLAVLA | CA6 |
| 110 | TVDGKSFPSELHLVHWNAKKYSTFGE- | -AASAPDGLAVVG | CA7 |
| 130 | TVNFKAFPMELHLIHWNSTLFGSIDE- | -AVGKPHGIAIIA | CA? |

FIGURE 3D

| | | | | | | | | |
|---|---|---|---|---|---|---|---|---|
| 186 | LFVNVASTSNPF | - | LSRLLNRDTITRISYKNDAYFLQDLSL | 2059155 |
| 146 | VLMKVGEA | -NPK- | LQKVL--DALQAIHKTKGKRAPFTNFDP | CA1 |
| 144 | IFLKVGSA | -KPG- | LQKVV--DVLDSIHKTKGKSADFTNFDP | CA2 |
| 144 | IELKIGHE | -NGE- | FQIFL--DALDKIKTKGKEAPFTKFDP | CA3 |
| 168 | FLVEAGTQVNEG | - | EALSNIPKPEMSTTMAESSL | CA4 |
| 182 | VFLKLGAH | -HQT- | LQRLV--DILPEIHKDARAAMRPFDP | CA5 |
| 164 | AFVEVKNYPENTYYSNFI | - | SHLANLKYPGQRTTLTGLDV | CA6 |
| 148 | VFLETGDE | -HPS- | MNRLT--DALYMVRFKGTKAQFSCFNP | CA7 |
| 168 | LFVQIGKE | -HVG- | LKAVT--EILQDIQYKGKSKTIPCFNP | CA? |

| | | | | | | | | |
|---|---|---|---|---|---|---|---|---|
| 225 | ELLFPE | -SF- | --G | FITYQGSLSTPPCSETVTWILIDRAL | 2059155 |
| 182 | STLLPS | -SL- | --D | FWTYPGSLTHPPLYESVTWIHICKESI | CA1 |
| 180 | RGLLPE | -SL- | --D | YWTYPGSLTTPPLLECVTWIVLKEPI | CA2 |
| 180 | SCLFPA | -CR- | --D | YWTQGSFTTPPCEEKVVWLLLKEPM | CA3 |
| 205 | LDLLPKEEKL | -RHY- | FRYLGSLTTPPTCDEKVVWTVFREPI | CA4 |
| 218 | STLLLPT | -CW- | --D | YWTYHGSLTTPPLTENVHWTIHQKEPV | CA5 |
| 202 | QDMLPR | -NL- | --Q | HYYTYHGSLTTPPCTEENVHWFVLADFV | CA6 |
| 184 | KCLLPA | -SR- | --H | YWTYPGSLTTPPLSESVTWIVLREPI | CA7 |
| 204 | NTLLPD | -PLLRD- | YWVYEGSLTIPPCSEGVTWILFRYPL | CA? |

FIGURE 3E

| | | | | | | | | | | | | | | | | | | | | | |
|---|---|---|---|---|---|---|---|---|---|---|---|---|---|---|---|---|---|---|---|---|---|
| 260 | N I T S L Q M H S L | – | – | – | – | – | – | – | – | – | – | – | – | – | – | – P P S Q I F Q | 2059155 |
| 217 | S V S S E Q L A Q F | R L L | – | – | – | – | – | – | – | – | – | – | – | – | – | A | V | CA1 |
| 215 | S V S S E Q V L K F | – | – | – | – | – | – | – | – | – | – | – | – | – | – | E | E | CA2 |
| 215 | T V S S D Q M A K L | – R S L L S N V E G D N | – | – | – | – | – | – | – | – | – | – | – | P | V | CA3 |
| 243 | Q L H R E Q I L A F S Q K L Y | – R K L N F N G E G E P | – | – | – | – | – | – | – | – | – | – | – | E | Q | CA4 |
| 253 | E V A P S Q L S A F | – R T L L S S A E N E P | – | – | – | – | – | – | – | – | – | – | E | E | CA5 |
| 238 | K L S R T Q V W K L E N S L L | – | – | – | – | – | – | – | – | – | – | – | – | – | N | K | CA6 |
| 219 | C I S E R Q M G K F | – | – | – | – | – | – | – | – | – | – | – | – | – | – | R | I | CA7 |
| 241 | T I S Q L Q I E E F | – R S L L F T S E D D E | – | – | – | – | – | – | – | – | – | – | – | G | CA? |
| | | – | – | – R L | – R T H V K G A E L V E G C D | | | | | | | | | | | | |
| 283 | S L S | – | – G N S R P L Q P L A H R A L R G N R D P R H P E R R C R G P N Y | – | – R | – | – | 2059155 |
| 240 | P M Q | – | – H N N R P T Q P L K G R T V R A S | – | – | – | – | – | – | – | – | – | – | – | CA1 |
| 238 | L M V | – | – D N W R P A Q P L K N R Q I K A S | – | – | – | – | – | – | – | – | – | – | – | CA2 |
| 238 | P L V | – | – S N W R P A Q P I H N R V V R A S | – | – | – | – | – | – | – | – | – | – | – | CA3 |
| 263 | T V S M K D N V R P L Q Q L G Q R T V I K S G A P G R P | – | – | – | – | – L P W A | – | CA4 |
| 276 | M M V | – | – N N Y R P L M N R K V W A S | – | – | – | – | – | – | – | – | – | – | – | CA5 |
| 258 | T I H | – | – N D Y R R T Q P L K H R | – V V E S N F P N Q E | – | – | Y | – T | CA6 |
| 242 | H M V | – | – N N F R P P Q P L K G R V V K A S | – | – | – | – | – | – | – | – | – | – | – | CA7 |
| 269 | I L G | – | – D N F R P T Q P L S D R V I R A A | – | – | – | – | – | – | – | – | – | – | – | CA? |

FIGURE 3F

| | | | | | | | | | | | | | | | | | | | | | | | | | | |
|---|---|---|---|---|---|---|---|---|---|---|---|---|---|---|---|---|---|---|---|---|---|---|---|---|---|---|
| 2059155 | 319 | L | H | V | D | - | - | - | - | - | - | - | - | - | - | - | G | V | P | - | - | - | H | G | - | R | - |
| CA1 | 260 | L | - | - | - | - | - | - | - | - | - | - | - | - | - | - | - | - | - | - | - | - | - | - | - | F | - |
| CA2 | 258 | L | - | - | - | - | - | - | - | - | - | - | - | - | - | - | - | - | - | - | - | - | - | - | - | F | K |
| CA3 | 258 | L | - | - | - | - | - | - | - | - | - | - | - | - | - | - | - | - | - | - | - | - | - | - | - | F | K |
| CA4 | 295 | L | P | A | L | - | - | - | - | - | - | - | - | - | - | - | - | - | - | - | - | - | - | - | - | F | R |
| CA5 | 296 | L | G | S | E | F | Q | F | Y | L | H | K | I | E | E | I | L | D | Y | L | R | R | A | - | - | F | - |
| CA6 | 285 | L | G | P | M | L | A | C | L | L | A | G | F | L | - | - | - | - | - | - | - | - | - | - | - | F | - |
| CA7 | 262 | L | - | - | - | - | - | - | - | - | - | - | - | - | - | - | - | - | - | - | - | - | - | - | - | F | R | A |
| CA? | 289 | L | - | - | - | - | - | - | - | - | - | - | - | - | - | - | - | - | - | - | - | - | - | - | - | F | Q |

Additional column for CA5: Q A T N E G T R S

CARBONIC ANHYDRASE VIII

FIELD OF THE INVENTION

This invention relates to nucleic acid and amino acid sequences of a novel carbonic anhydrase isoform and to the use of these sequences in the diagnosis, prevention, or treatment of circulatory and neuronal diseases, inflammation, and cancer.

BACKGROUND OF THE INVENTION

Carbonic anhydrase (CA), also called carbonate dehydratase, catalyzes the hydration of carbon dioxide in the reaction $H_2O+CO_2 \leftrightarrows HCO_3^- +H^+$. It accelerate, this reaction by a factor of over $10^6$ by virtue of a zinc ion located in a deep cleft about 15 Å below the protein's surface and coordinated to the imidazole groups of three His residues. Water bound to the zinc ion is rapidly converted to $HCO_3^-$.

CA is crucial to the maintenance of pH in body fluids. A large quantity of acids enter the body, from both dietary and metabolic sources and consume intracellular and extracellular buffers. $HCO_3^-$ is the most important buffer in the intracellular compartment. CA is needed to regenerate and reclaim $HCO_3^-$. In the kidneys, the reabsorption of $HCO_3^-$ in the renal proximal tubule occurs via CA, which combines $CO_2$ with the $OH^-$ ion that results from the splitting of water. The resulting $HCO_3^-$ moves across the peritubular cell membrane to enter the extracellular $HCO_3^-$ pool. The $H^+$ secreted into the tubule lumen combines with a filtered $HCO_3^-$, forming $H_2CO_3$, which is later dehydrated to form $CO_2$ that diffuses into peritubular blood, leaving a reclaimed $HCO_3^-$ ion. So essential is the maintenance of buffering capacity that in chronic renal failure, bone tissue may be used as a source of $HCO_3^-$ to replace that lost in the urine. In red blood cells, CA speeds the reaction of water with carbon dioxide from tissues so that large amounts of $CO_2$ are taken up before the blood leaves the capillaries. CA may be involved in the regulation of vascular tonus, since CA activity is inhibited by vasodilating drugs such as nitroglycerin in parallel with their vasodilating effect (Puscas, I. et al. (1997) Am. J. Hypertens. 10(1):124–128). Carbonic anhydrase is one of the key enzymes responsible for the secretion of cerebrospinal fluid. This secretion increases dramatically during postnatal life in mammals. The expression of carbonic anhydrase is developmentally regulated in several cells, such as erythrocytes and striated muscle fibers (Catala, M. (1997) Childs Nerv. Syst. 13(7):364–368). CA in the extracellular boundary layer of sarcolemma facilitates $CO_2$ transport via the catalyzed hydration of $CO_2$, thus maintaining the $PCO_2$ gradient across the sarcolemma, and $H^+$ released in that reaction protonate excreted $NH_3^-$ which helps maintain the $PNH_3$ gradient (Henry, R. P. et al. (1997) Am. J. Physiol. 262(6/2):R1754–R1761). In the placenta, carbonic anhydrase may provide ions for exchange with $Na^+$, $K^+$, and $Cl^-$ in transepithelial movement of ions and fluid, as well as facilitating $CO_2$ diffusion. It can also be active in intermediary metabolism, such as glucorieogenesis, urea, and fatty acid synthesis (Ridderstrale, Y. (1997) Microsc. Res. Tech. 38(1–2): 115–124).

Kinetic studies of CA folding have indicated the occurrence of con formational intermediates. Human CAI contains a cysteine residue, Cys212, which is unavailable for alkylation in the native state, but can be specifically modified with iodoacetate in the unfolded state. Bergenhem et al. concluded that the Cys-containing beta strand is part of a nucleation center that forms during the folding process. The beta strand is also partly involved in forming the bottom of the active site cavity (Bergenhem, N. et al. (1989) Int. J. Pept. Prot. Res. 33(2):140–145). Within the active site Leu198, Thr199 and His200 have been identified as important for binding of sulfonamide inhibitors which interact with the zinc ion (Chakravarty, S. et al. (1994) J. Mol. Biol. 243(2):298–309). Spectroscopic evidence has indicated that histamine, a CA activator, also binds to the entrance of the active site but not to the metal ion (Briganti, F. et al. (1997) Biochemistry 36(34):10384–10392).

Eight enzymatic and evolutionarily related forms of carbonic anhydrase are currently known to exist in humans: three cytosolic isozymes (CAI, CAII, and CAIII, two membrane-bound forms (CAIV and CAVII), a mitochondrial form (CAV), a secreted salivary form (CAVI) and a yet uncharacterized isozyme. Isoforms show a characteristic motif. (See, e.g., http//expasy.hcuge.ch). Though the isoenzymes CAI, CAII, and bovine CAIII have similar secondary structure and polypeptide-chain fold, CAI has 6 tryptophans, CAII has 7 and CAIII has 8 (Boren, K. et al. (1996) Protein Sci. 5(12):2479–2484). CAII is the predominant CA isoenzyme in the brain of mammals.

Inhibition and activation of CA provide information about CA stricture and activity. Vasodilating prostaglandins E1, E2 and I2 inhibit CA in vitro and in vivo and may inhibit the involvement of CA in gastric acid secretion. Nonsteroidal anti-inflammattory drugs which reduce the activity of cyclooxygenase and prostaglandin production have also been observed to activate CAI and CAII in a dose-dependent noncompetitive manner. The pre-prostaglandin cyclooxygenase appears to maintain an inverse relationship with CA, probably mediated by the pH variations associated with carbonic anhydrase activity (Puscas, I. (1996) J. Pharmacol. Exp. Ther. 277(3):1464–1466). Both prostaglandins E2 and I2 inhibit gastric acid output. Prostaglandin E2 inhibits egress of norepinephrine from sympathetic nerve terminals.

Histamine is a CA activator. Histamine is released in essentially every tissue of the body when it becomes damaged, inflamed, or is subject to allergic reaction. Histamine stimulates gastric acid secretion, increases smooth muscle contraction, and has a powerful vasodilator effect, to the extent that the increased capillary porosity it causes may lead to edema. The prostaglandins, which are equally ubiquitous and important in inflammation processes, include vasodilating and some vasoconstricting agents, and function in circulatory control by their action on the smooth muscle of the vessel wall (Isselbacher, K. J. et al. (1994) *Harrison's Principles of Internal Medicine*, McGraw-Hill, New York, N.Y.).

A number of disease states are marked by variations in CA activity The concentration of CAII in the cerebrospinal fluid (CSF) appears to mark disease activity in patients with brain damage. High CA concentrations have been observed in patients with brain infarction. Patients with transient ischaemic attack, multiple sclerosis, or epilepsy usually have CAII concentrations in the normal range, but higher CAII levels have been observed in the CSF of those with central nervous system infection, demertia, or trigeminal neuralgia (Parkkila, A. K. et al. (1997) Eur. J. Clin. Invest. 27(5): 392–397). Colonic adenomas and adenocarcinomas have been observed to fail to stain for CA, whereas nonneoplastic controls showed CAI and CAII in the cytoplasm of the columnar cells lining the upper half of colonic crypts. The neoplasms show staining patterns similar to less mature cells lining the base of normal crypts (Gramlich T. L. et al. (1990) Arch. Pathol. Lab. Med. 114(4):415–419). Deficiency of CAII has been identified as the primary defect in osteopetrosis, a rare metabolic bone disease characterized by increase in skeletal mass due to a defect in development or function of the osteoclasts (Felix, R. et al. (1996) Eur. J. Endocrinol. 134(2):143–156).

Therapeutic interventions in a number of diseases involve altering CA activity. Ophthalmic disorders are commonly treated with carbonic anhydrase inhibitors such as acetazolamide. Topical preparations such as eye drops have been suggested as an additional and safer treatment for patients with uncontrolled medical glaucoma (Centofanti, M. (1997) Pharmacol. Res. 35(5): 481–485). Carbonic anhydrase inhibitors are also used to treat chronic renal failure (Suki, W. N. (1997) Kidney Int. Suppl. 59:S33–S35), Parkinson's Disease and tardive dyskinesia (Cowen, M. A. et al. (1997) J. Clin. Pharmacol. 17(3):190–193) epileptic seizures uncontrolled by other marketed agents (Reiss, W. G. (1 996) Ann. Pharmacother. 30(5):514–519). Adverse effects of acetazolamide treatment include kidney stones, metabolic acidosis, lethargy, appetite suppression, paresthesias, and rare blood dyscrasias.

CA activity can be particularly useful as an indicator of long-term disease condition, since the enzyme reacts relatively slowly to physiological changes. CAI and zinc concentrations have been observed to decrease in hyperthyroid Graves' disease (Yoshida, K. (1996) Tohoku J Exp Med 178(4):345–356) and glycosylated CAI is observed in diabetes mellitus (Kondo, T. et al. (1987) Clin. Chim. Acta 166(2–3):227–236). A positive correlation has been observed between CAI and CAII reactivity and endometriosis (Brinton, D. A. et al. (1996) Ann. Clin. Lab. Sci. 26(5):409–420; D'Cruz, O. J. et al. (1996) Fertil. Steril. 66(4):547–556).

The discovery of a new carbonic anhydrase and the polynucleotides encoding it satisfies a need in the art by providing new compositions which are useful in the diagnosis, prevention or treatment of circulatory and neuronal diseases, inflammatior, and cancer.

SUMMARY OF THE INVENTION

The invention features a substantially purified polypeptide, carbonic anhydrase VIII (CAVIII), comprising the amino acid sequence of SEQ ID NO:1 or a fragment of SEQ ID NO:1.

The invention further provides a substantially purified variant of CAVIII having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at Least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding CAVIII under conditions suitable for the expression of the polypeptide; and (b) recovering the polypeptide from the host cell culture.

The invention also provides a pharmaceutical composition comprising a substantially purified CAVIII having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing inflammation comprising administering to a subject in need of such treatment an effective amount of a pharmaceutical composition comprising purified CAVIII.

The invention also provides a method for treating or preventing inflammation comprising administering to a subject in need of such treatment an effective amount of an antagonist to CAVIII.

The invention also provides a method for treating or preventing circulatory disorders comprising administering to a subject in need of such treatment an effective amount of a pharmaceutical composition comprising purified CAVIII.

The invention also provides a method for treating or preventing circulatory disorders comprising administering to a subject in need of such treatment an effective amount of an antagonist to CAVIII.

The invention also provides a method for treating or preventing neuronal disorders comprising administering to a subject in need of such treatment an effective amount of an antagonist to CAVIII.

The invention also provides a method for treating or preventing cancer comprising administering to a subject in need of such treatment an effective amount of an antagonist to CAVIII.

The invention also provides a method for detecting a polynucleotide encoding CAVIII in a biological sample containing nucleic acids, the method comprising the steps of: (a) hybridizing the complement of the polynucleotide sequence which encodes the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding CAVIII in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of CAVIII. The alignment was produced using MacDNASIS PRO™ software (Hitachi Software Engineering Co. Ltd. San Bruno, Calif.).

FIG. 2 shows the amino acid sequence alignments between CAVIII (2059155; SEQ ID NO:1) and a carbonic anhydrase-like protein (GI 1532042; SEQ ID NO:3), produced using the multi sequence alignment program of DNASTAR™ software (DNASTAR Inc, Madison Wis.).

FIGS. 3A, 3B, 3C, 3D, 3E, and 3F show the amino acid and consensus (G144–H162) sequence alignments between CAVIII (2059155; SEQ ID NO:1) and the identified isoforms of carbonic anhydrase (CA1, P00915; CA2, P00918; CA3, P07451; CA4, P22748; CA5, P35218; CA6, P23280; CA7, P43166; and CA?[uncharacterized], P35219), produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to these described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the nvention is not entitled to antedate such disclosure by virtue of prior invention.

DEFINITIONS

CAVIII, as used herein, refers to the amino acid sequences of substantially purified CAVIII obtained from any species, particularly mammalian, including bovine, ovine, porcine, murine, equine, and preferably human, from any source whether natural, Synthetic, semi-synthetic, or recombinant.

The term "agonist", as used herein, refers to a molecule which, when bound to CAVIII, increases or prolongs the duration of the effect of CAVIII. Agonists may include proteins, nucleic acids, carbohydrates, or any other molecules which bind to and modulate the effect of CAVIII.

An "allele" or "allelic sequence", as used herein, is an alternative form of the gene encoding CAVIII. Alleles may result from at least one mutation in the micleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding CAVIII as used heroin include those with deletions, insertions, or substitutions of different nucleotides resulting in a polynucleotide that encodes the same or a functionally equivalent CAVIII. Included within this definition are polymorphisms which may or may not be readily detectable using a particular oligonucleotide probe of the polynucleotide encoding CAVIII, and improper or unexpected hybridization to alleles, with a locus other than the normal chromosomal locus for the polynucleotide sequence encoding CAVIII. The encoded protein may also be "altered" and contain deletions, insertions, or substitutions of amino acid residues which produce a silent change and result in a functionally equivalent CAVIII. Deliberate amino acid substitutions may be made on the basis of similarity in polarity, charge, solubility, hydrophobicity, hydrophilicity, and/or the amphipathic nature of the residues as long as the biological or immunological activity of CAVIII is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of CAVIII are preferably about 5 to about 15 amino acids in length and retain the biological activity or the immunological activity of CAVIII. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chair reaction (PCR) technologies well known in the art (Dieffenbach, C. W. and G. S. Dveksler (1995) PCR *Primer, a Laboratory Manual*, Cold Spring Harbor Press, Plainview, N.Y.).

The term "antagonist" as used herein, refers to a molecule which, when bound to CAVIII, decreases the amount or the duration of the effect of the biological or immunological activity of CAVIII. Antagonists may include proteins, nucleic acids, carbohydrates, antibodies or any other molecules which decrease the effect of CAVIII.

As used herein, the term "antibody" refers to intact molecules as well as fragments thereof, such as Fa, F(ab')$_2$, and Fv, which are capable of binding the epitopic determinant. Antibodies that bind CAVIII polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic CAVIII, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding CAVIII (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCC, Madison, Wis.). Some sequences have been both extended and assembled to produce the consensus sequence .

The term "correlates with expression of a polynucleotide", as used herein, indicates that the detection of the presence of ribonucleic acid that is similar to SEQ ID NO:2 by northern analysis is indicative of the presence of mRNA encoding CAVIII in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to CAVIII or the encoded CAVIII. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in orcLer to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of CAVIII. For example, modulation may cause an increase or a decrease in protein activity, binding characteristics, or any other biological, functional or immunological properties of CAVIII.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length CAVIII and fragments thereof.

The term "sample", as used herein, is used in its broadest sense. A biological sample suspected of containing nucleic acid encoding CAVIII, or fragments thereof, or CAVIII itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of form amide, or raising the hybridization temperature.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of CAVIII, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human carbonic anhydrase (hereinafter referred to as "CAVIII"), the polynucleotides encoding CAVIII, and the use of these compositions for the diagnosis, prevention, or treatment of circulatory and neuronal diseases, inflammation, and cancer.

Nucleic acids encoding the CAVIII of the present invention were first identified in Incyte Clone 2059155 from the human ovary-derived cDNA library OVARNOT03 using a computer search for amino acid sequence alignments. A consensus sequence, SEQ ID NO:2, was derived from the following overlapping and/or extended nucleic acid sequences: Incyte Clones 1365108 (SCORNON02), 1890331 (BLADTUT07), and 1383776 (BRAITUT08).

In one embodiment, the invention encompasses a polypeptide comprising the amino acid sequence of SEQ ID NO:1, as shown in FIG. 1. CAVIII is 328 amino acids in length and has: a potential amidation site at residue V64; potential glycosylation sites at residues N118, N170, and N260; a potential cAMP-dependent protein kinase phorphorylation site at residue S69; potential Casein kinase II phosphorylation sites at residues S36, S69), and T91; and potential protein kinase C phosphorylation sites at residues S36, T103, S127, S211, and S268. As shown in FIG. 2, CAVIII has chemical and structural homology with a carbonic anhydrase-like protein (GI 1532042; SEQ ID NO:3). CAVIII and the carbonic anhydrase-like protein share 83% identity.

As shown in FIG. 3, CAVIII has chemical and structural homology with previously identified CA isoforms. The CA consensus sequence is highly conserved from residue 145–161 of SEQ ID NO:2. CAVIII differs from the consensus sequence at only 1 residue (Q159). A potential zinc-ligand H residue at 162 is conserved as well. Significant conservation is also noted at residues T236–254 and residues N287–297.

Northern analysis shows the expression of this sequence in various libraries, including brain tissue (cerebellum, glial, choroid plexus, hippocampus, right frontal, midline frontal, temporal lobe, astrocytoma), uterus, ovary, breast, adrenal gland, bladder, colon, pancreas and thyroid; at least 48% of these libraries are cancerous, at least 48% of these libraries are nervous-system derived, and at least 22% are derived from female reproductive tissues.

The invention also encompasses CAVIII variants. A preferred CAVIII variant is one having at least 80%, and more preferably at least 90%, amino acid sequence identity to the CAVIII amino acid sequence (SEQ ID NO:1) and which retains at least one biological, immunological or other functional characteristic or activity of CAVIII. A most preferred CAVIII variant is one having at least 95% amino acid sequence identity to SEQ ID NO:1 and which retains at least one biological, immunological or other functional characteristic or activity of CAVIII.

The invention also encompasses polynucleotides which encode CAVIII. Accordingly, any nucleic acid sequence which encodes the amino acid sequence of CAVIII can be used to produce recombinant molecules which express CAVIII. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of polynucleotide sequences encoding CAVIII, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring CAVIII, and all such variations are to be considered as being specifically disclosed.

Although nucleotide sequences which encode CAVIII and its variants are preferably capable of hybridizing to the nucleotide sequence of the naturally occurring CAVIII under appropriately selected conditions of stringency, it may be advantageous to produce nucleotide sequences encoding CAVIII or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CAVIII and its derivatives without altering; the encoded amino acid sequences include the production of RNA transcripts having more desirable properties, such as a greater half-life, than transcripts produced from the naturally occurring sequence.

The invention also encompasses production of DNA sequences, or fragments thereof, which encode CAVIII and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding CAVIII or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding CAVIII may be extended utilizing a partial nucleotide sequence and employing various methods known in the art to letect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The methcd uses several restriction enzymes to generate a suitable fragment in the known region of a gene. The fragment is then circularized by intramolecular ligation and used as a PCF. template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode CAVIII may be used in recombinant DNA molecules to direct expression of CAVIII, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express CAVIII.

As will be understood by those of skill in the art, it may be advantageous to produce CAVIII-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter CAVIII encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding CAVIII may be ligated to a heterologous sequence to encode a fusion protein. For example, to screen peptide libraries for inhibitors of CAVIII activity, it may be useful to encode a chimeric CAVIII protein that can be recognized by a commercially available antibody. A fusion protein may also be engineered to contain a cleavage site located between the CAVIII encoding sequence and the heterologous protein sequence, so that CAVIII may be cleaved and purified away from the heterologous moiety.

In another embodiment, sequences encoding CAVIII may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of CAVIII, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of CAVIII, or any part thereof, may be altered during direct synthesis and/or combined using chemical methods with sequences from other proteins, or any part thereof, to produce a variant polypeptide.

In order to express a biologically active CAVIII, the nucleotide sequences encoding CAVIII or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding CAVIII and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding CAVIII. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or aninial cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding CAVIII, vectors based on SV40 or EBV may be used with an appropriate selectable marker.

In bacterial systems, a number of expression vectors may be selected depending upon the use intended for CAVIII. For example, when large quantities of CAVIII are needed for the induction of antibodies, vectors which direct high level expression of fusion proteins that are readily purified may be used. Such vectors include, but are not limited to, the multifunctional E. coli cloning and expression vectors such as Bluescript® (Stratagene), in which the sequence encoding CAVIII may be ligated into the vector in frame with sequences for the amino-terminal Met and the subsequent 7 residues of β-galactosidase so that a hybrid protein is produced; pIN vectors (Van Heeke, G. and S. M. Schuster (1989)) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression oil sequences encoding CAVIII may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or seat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill., New York, N.Y.; pp. 191–196.

An insect system may also be used to express CAVIII. For example, in one such system, Autographa californica nuclear polyhedrosis virus (AcNPV) is used as a vector to express foreign genes in *Spodoptera frugiperda* cells or in Trichoplusia larvae. The sequences encoding CAVIII may be cloned into a non-essential region oi the virus, such as the polyhedrin gene, and placed under control of the polyhedrin promote. Successful insertion of CAVIII will render the polyhedrin gene inactive and produce recombinant virus lacking coat protein. The recombinant viruses may then be used to infect, for example, *S. frugiperda* cells or Trichoplusia larvae in which CAVIII may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding CAVIII may be ligated into an adenovirus transcription/translation complex consisting of the late promoter and tripartite leader sequence. Insertion in a non-essential E1 or E3 region of the viral genome may be used to obtain a viable virus which is capable of expressing CAVIII in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding CAVIII. Such signals include the ATG initiation colon and adjacent sequences. In cases where sequences encoding CAVIII, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express CAVIII may be transformed using expression vectors which may contain viral origins of replication and/or endogenous expression elements and a selectable marker gene on the same or on a separate vector.

Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding CAVIII is inserted within a marker gene sequence, transformed cells containing sequences encoding CAVIII can be identified by the absence of marker gene function. Alternatively, a marker gene can be placed in tandem with a sequence encoding CAVIII under the control of a single promoter. Expression of the marker gene in response to induction or selection usually indicates expression of the tandem gene as well.

Alternatively, host cells which contain the nucleic acid sequence encoding CAVIII and express CAVIII may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding CAVIII can be detected by DNA-DNA or DNA-RNA hybridization or amplification using probes or fragments or fragments of polynucleotides encoding CAVIII. Nucleic acid amplification based assays involve the use of oligonucleotides or oligomers based on the sequences encoding CAVIII to detect transformants containing DNA or RNA encoding CAVIII.

A variety of protocols for detecting and measuring the expression of CAVIII, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on CAVIII is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding CAVIII include oligolabeling, nick translation, end-labeling or PCR amplification using a labeled nucleotide. Alternatively, the sequences encoding CAVIII, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding CAVIII may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode CAVIII may be designed to contain signal sequences which direct secretion of CAVIII through a prokaryotic or eukaryotic cell membrane. Other constructions may be used to join sequences encoding CAVIII to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and CAVIII may be used to facilitate purification. One such expression vector provides for expression of a fusion protein containing CAVIII and a nucleic acid encoding 6 histidine residues preceding a thioredoxin or an enterokiriase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying CAVIII from the fusion protein. A discussion of vectors which contain fusion proteins is provided in Kroll, D. J. et al. (1993; DNA Cell Biol. 12:441–453).

In addition to recombinant production, fragments of CAVIII may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of CAVIII may be chemically synthesized separately and combined using chemical methods to produce the full length molecule.

THERAPEUTICS

Chemical and structural homology exists between/among CAVIII and other carbonic anhydrase isoforms. Therefore, CAVIII appears to play a role in circulatory and neuronal diseases, inflammation, and cancer.

The expression of carbonic anhydrase is closely associated with inflammation. Histamine and nonsteroidal anti-inflammatory agents activate CA, whereas the vasodilating prostaglandins E1, E2 and 12 inhibit CA. Where CA promotes inflammation, it is beneficial to decrease the expression of CAVIII. Where CA decreases inflammation, it is beneficial to provide the protein or increase the expression of CAVIII.

Therefore, in one embodiment, CAVIII or a fragment or derivative, thereof may be administered to a subject to prevent or treat inflammation which results from inhibition of CA. In particular, such inflammation may be associated with, but not limited to, conditions or disorders such as endometriosis, glaucoma, Graves' disease, gastric ulcer, chronic renal failure, osteopetrosis, AIDS, Addison's disease, adult respiratory distress syndrome, allergies, anemia, asthma, atherosclerosis, bronchitis, cholecystitis, Crohn's disease, disruptions of the estrous cycle, disruptions of the menstrual cycle, ulcerative colitis, atopic dermatitis, dermatomyositis, diabetes mellitus, emphysema, erythema nodosum, atrophic gastritis, gingivitis, glomerulonephritis, gout, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, renal failure, renal tubular acidosis, rheumatoid arthritis, scleroderma, Sjögren's syndrome, autoimmune thyroiditis, ulcers; complications of cancer, hemodialysis, and extracorporeal circulation; viral, bacterial, fungal, parasitic, protozoal, and helminthic infections; and trauma.

In another embodiment, a vector capable of expressing CAVIII, or a fragment or a derivative thereof, may also be administered to a subject to treat inflammation including, but not limited to, disorders associated with inflammation which results from inhibition of CA.

In another embodiment, an agonist which modulates the activity of CAVIII may also be administered to a subject to treat inflammation including, but not limited to, disorders that are associated with inflammation which results from inhibition of CA.

In another embodiment antagonists which decrease the activity of CAVIII may be administered to a subject to prevent or treat inflammation which results from activation of CA or is promoted by CA. In particular, such inflammation may be associated with, but not limited to, conditions or disorders such as endometriosis, glaucoma, Graves' disease, gastric ulcer, chronic renal failure, osteopetrosis, AIDS, Addison's disease, adult respiratory distress syndrome, allergies, anemia, asthma, atherosclerosis, bronchitis, cholecystitis, Crohn's disease, disruptions of the estrous cycle, disruptions of the menstrual cycle, ulcerative colitis, atopic dermatitis, dermatomyositis, diabetes mellitus, emphysema, erythema nodosum, atrophic gastritis, gingivitis, glomerulonephritis, gout, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, renal failure, renal tubular acidosis, rheumatoid arthritis, scleroderma, Sjögren's syndrome, autoimmune thyroiditis, ulcers; complications of cancer, hemodialysis, and extracorporeal circulation; viral, bacterial, fungal, parasitic, protozoal, and helminthic infections; and trauma.

In another embodiment, a vector expressing the complement of the polynucleotide encoding CAVIII may be administered to a subject to treat or prevent inflammation including, but not limited to, disorders associated with inflammation which results from activation of CA.

The expression of carbonic anhydrase is closely associated with circulatory regulation. In a circulatory disorder which is associated with the activation of disease processes by CA, it is beneficial to decrease the expression of CAVIII in a subject afflicted with the disorder. In a circulatory disorder which is associated with the inhibition of CA, it is beneficial to provide the protein or increase the expression of CAVIII in a subject afflicted with the disorder.

Therefore, in another embodiment, antagonists of CAVIII may be administered to a subject to prevent or treat a circulatory disorder, any disorder involving circulation of the blood or lymph, which is associated with CA activation or promoted by CA. Such circulatory disorders include, but are not limited to, hypertension, acidosis, alkylosis, diabetic nephropathy, edema, glaucoma, glomerular disorders, hypercalemia, heart failure, hypotension, and shock.

In another embodiment, a vector expressing the complement of the polynucleotide encoding CAVIII may be administered to a subject to treat or prevent a circulatory disorder including, but not limited to, those described above.

In another embodiment, CAVIII or a fragment or derivative thereof may be administered to a subject to prevent or treat a circulatory disorder which is associated with inhibition of CA. Such circulatory disorders include, but are not limited to, hypertension, acidosis, alkylosis, diabetic nephropathy, edema, glaucoma, glomerular disorders, hypercalemia, heart failure, hypotension, and shock.

In another embodiment, a vector capable of expressing CAVIII, or a fragment or a derivative thereof, may also be administered to a subject to treat a circulatory disorder including, but not limited to, those described above.

In another embodiment, an agonist which modulates the activity of CAVIII may also be administered to a subject to treat a circulatory disorder including, but not limited to, those described above.

The expression of carbonic anhydrase is closely associated with neuronal disorders. Decreased extracellular levels of calcium increase neuron excitability. In neuronal disorders, it is beneficial to decrease the expression of CAVIII.

Therefore, in another embodiment, antagonists of CAVIII may be administered to a subject to prevent or treat a neuronal disorder. Such neuronal disorders include, but are not limited to, epilepsy, tardive dyskinesia, brain infarction, Parkinson's Disease, Alzheimer's Disease, ischaemia, stroke, akathesia, Alzheimer's disease, amnesia, amyotrophic lateral sclerosis, bipolar disorder, catatonia, cerebral neoplasms, dementia, depression, Down's syndrome, dystonias, epilepsy, Huntington's disease, multiple sclerosis, neurofibromatosis, Parkinson's disease, paranoid psychoses, schizophrenia, and Tourette's disorder.

In another embodiment, a vector expressing the complement of the polynucleotide encoding CAVIII may be administered to a subject to treat or prevent a neuronal disorder including, but not limited to, those described above.

In another embodiment, antagonists of CAVIII may be administered to a subject to prevent or treat a cancer.

Cancers may include, but are not limited to, adenocarcinoma, lymphoma, melanoma, myeloma, sarcoma, teratocarcinoma, cancer of the adrenal gland, bladder, bone, bone marrow, brain, breast, cervix, gall bladder, ganglia, Gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding CAVIII may be administered to a subject to treat or prevent a cancer including, but not limited to, those described above.

In any of the above embodiments in which an antagonist of CAVIII is administered, an antibody which specifically binds CAVIII may be used directly as an antagonist or indirectly as a targeting or delivery mechanism for bringing a pharmaceutical agent to cells or tissue which express CAVIII.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of CAVIII may be produced using methods which are generally known in the art. In particular, purified CAVIII may be used to produce antibodies or to screen libraries of pharmaceutical agents to identify those which specifically bind CAVIII.

Antibodies to CAVIII may be generated using methods that are well known in the art. Such antibodies may include, but are not limited to, polyclonal, monoclorial, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with CAVIII or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to CAVIII have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of CAVIII amino acids may be fused with those of another protein such as keyhole limpet hemocyanin and antibody produced against the chimeric molecule.

Monoclonal antibodies to CAVIII may be prepared using any technique which provides for the production of antibody molecules by continuous cell line, in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce CAVIII-specific single chain antibodies. Antibodies with related specificity, but of distinct idiotypic composition, may be generated by chain shuffling from random combinatorial immunoglobin libraries (Burton D. R. (1991) Proc. Nati. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for CAVIII may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CAVIII and its specific antibody. A two-site, monoclonal-based immunoassay utilizing monoclonal antibodies reactive to two non-interfering CAVIII epitopes is preferred, but a competitive binding assay may also be employed (Maddox, supra).

In another embodiment of the invention, the polynucleotides encoding CAVIII, or any fragment or complement thereof, may be used for therapeutic purposes. In one aspect, the complement of the polynucleotide encoding CAVIII may be used in situations in which it would be beneficial to block the transcription of the mRNA. In particular, cells may be transformed with sequences complementary to polynucleotides encoding CAVIII. Thus, complementary molecules or fragments may be used to modulate CAVIII activity, or to achieve regulation of gene function. Such technology is now well know in the art, and sense or antisense oligonucleotides or larger fragments, can be designed from various locations along the coding or control regions of sequences encoding CAVIII.

Expression vectors derived from retro viruses, adenovirus, herpes; or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding CAVIII. These techniques are described both in Sambrook et al. (supra) and in Ausubel et al. (supra).

Genes encoding CAVIII can be turned off by transforming a cell or tissue with expression vectors which express high levels of a polynucleotide or fragment thereof which encodes CAVIII. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding CAVIII (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publshing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding CAVIII.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CAVIII. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of CAVIII, antibodies to CAVIII, mimetics, agonists, antagonists, or inhibitors of CAVIII. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein filler, such as sugars, including lactose, sucrose, mannitol, or sorbitol;

starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrans appropriate to the particular barrier to be permeated are used in the formulation. Such penetrans are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of CAVIII, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example CAVIII or fragments thereof, antibodies of CAVIII, agonists, antagonists or inhibitors of CAVIII, which ameliorates the symptoms or condition. Therapeutic efficacy and toxicity may be determined by standard pharmaceutical procedures in cell culture or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating, a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind CAVIII may be used for the diagnosis of conditions or diseases characterized by expression of CAVIII, or in assays to monitor patients being treated with CAVIII, agonists, antagonists or inhibitors. The antibodies useful for diagnostic purposes may be prepared in the same manner as those described above for therapeutics. Diagnostic assays for CAVIII include methods which utilize the antibody and a label to detect CAVIII in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring CAVIII are known in the art and provide a basis for diagnosing altered or abnormal levels of CAVIII expression. Normal or standard values for CAVIII expression are established by combining body fluids or cell extracts taken from normal mammalian subjects, preferably human, with antibody to CAVIII under conditions suitable for complex formation The amount of standard complex formation may be quantified by various methods, but preferably by photometric, means. Quantities of CAVIII expressed in subject, control and disease, samples from biopsied tissues are compared with the standard values. Deviation between standard and subject values establishes the parameters for diagnosing disease.

In another embodiment of the invention, the polynucleotides encoding CAVIII may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CAVIII may be correlated with disease. The diagnostic assay may be used to distinguish between absence, presence, and excess expression of CAVIII, and to monitor regulation of CAVIII levels during therapeutic intervention.

In one aspect, hybridization with PCR probes which are capable of detecting polynucleotide sequences, including genomic sequences, encoding CAVIII or closely related molecules, may be used to identify nucleic acid sequences which encode CAVIII. The specificity of the probe, whether it is made from a highly specific region, e.g., 10 unique nucleotides in the 5' regulatory region, or a less specific region, e.g., especially in the 3' coding region, and the stringency of the hybridization or amplification (maiximal, high, intermediate, or low) will determine whether the probe identifies only naturally occurring sequences encoding CAVIII, alleles, or related sequences.

Probes may also be used for the detection of related sequences, and should preferably contain at least 50% of the nucleotides from any of the CAVIII encoding sequences. The hybridization probes of the subject invention may be DNA or RNA and derived from the nucleotide sequence of SEQ ID NO:2 or from genomic sequence including promoter, enhancer elements, and introns of the naturally occurring CAVIII.

Means for producing specific hybridization probes for DNAs encoding CAVIII include the cloning of nucleic acid sequences encoding CAVIII or CAVIII derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding CAVIII may be used for the diagnosis of conditions or disorders which are associated with expression of CAVIII. Examples of such conditions or disorders include: circulatory disorders such as hypertension, acidosis, alkylosis, diabetic nephropathy, edema, glaucoma, hypercalemia, heart failure, hypertension, hypotension, shock, acidosis, alkylosis, diabetic nephropathy, glaucoma, glomerular disorders, hypercalemia, heart failure, hypertension, hypo tension, shock; neuronal disorders such as epilepsy, tardive dyskinesia, brain infarction, Parkinson's Disease. ischaemia, stroke, akathesia, Alzheimer's disease, amnesia, amyotrophic lateral sclerosis, bipolar disorder, catatonia, cerebral neoplasms, dementia, depression, Down's syndrome, dystonias, epilepsy, Huntington's disease, multiple sclerosis, neurofibromatosis, Parkinson's disease, paranoid psychoses, schizophrenia, Tourette's disorder; cancers such as adenocarciroma, lymphoma, melanoma, myeloma, sarcoma, teratocarcinoma, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and inflammation associated with conditions and disorders such as endometriosis, glaucoma, Graves' disease, gastric ulcer, chronic renal failure, osteopetrosis, AIDS, Addison's disease, adult respiratory distress syndrome, allergies, anemia, asthma, atherosclerosis, bronchitis, cholecystitis, Crohn's disease, disruptions of the estrous cycle, disruptions of the menstrual cycle, ulcerative colitis, atopic dermatitis, dermatomyositis, diabetes mellitus, emphysema, erythema nodosum, atrophic gastritis, gingivitis, glomerulonephritis, gout, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, renal failure, renal tubular acidosis, rheumatoid arthritis, scleroderma, autoimmune thyroiditis, ulcers; complications of cancer, hemodialysis, extracorporeal circulation; viral, bacterial, fungal, parasitic, protozoal, and helminthic infections; and trauma.

The polynucleotide sequences encoding CAVIII may be used in Southern or northern analysis, dot blot, or other membrane-based technologies; in PCR technologies; or in dipstick, pin, ELISA assays or microarrays utilizing fluids or tissues from patient biopsies to detect altered CAVIII expression. Such qualitative or quantitative methods are well known in the art.

In a particular aspect, the nucleotide sequences encoding CAVIII may be useful in assays that detect activation or induction of various cancers, particularly those mentioned above. The nucleotide sequences encoding CAVIII may be labeled by standard methods, and added to a fluid or tissue sample from a patient under conditions suitable fDr the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding CAVIII in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of CAVIII, a normal or standard profile for expression is established. This may be accomplished by combining body fluids or cell extracts taken from normal subjects, either animal or human, with a sequence, or a fragment thereof, which encodes CAVIII, under conditions suitable for hybridization or amplification. Standard hybridization may be quantified by comparing the values obtained from normal subjects with those from an experiment where a known amount of a substantially purified polynuclectide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CAVIII may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitated the expression of CAVIII include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link CDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode CAVIII may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the locatior of the gene encoding CAVIII on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, CAVIII, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between CAVIII and the agent being, tested, may be measured.

Another technique for drug screening which may be used provides for high throughput screening of compounds having suitable binding affinity to the protein of interest as described in published PCT application WO84/03564. In this method, as applied to CAVIII large numbers of different small test compounds are synthesized on a solid substrate, such as plastic pins or some other surface. The test compounds are reacted with CAVIII, or fragments thereof, and washed. Bound CAVIII is then detected by methods well known in the art. Purified CAVIII can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CAVIII specifically compete with a test compound for binding CAVIII. In this manner, the antibodies can be used to detect the presence of any peptide which shares one or more antigenic determinants with CAVIII.

In additional embodiments, the nucleotide sequences which encode CAVIII may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I OVARNOT03 cDNA Library Construction

The OVARNOT03 library was constructed using 1 microgram of polyA RNA isolated from nontumorous ovarian tissue removed from a 43-year-old Caucasian female during a bilateral salpingo-oopherectomy (removal of the fallopian tubes and ovaries). Pathology for the associated tumor tissue indicated grade 2 mucinous cystadenocarcinoma. Staging biopsies and lymph nodes were negative for tumor. The patient presented with stress incontinence. Patient history included mitral valve disorder, pneumonia, and viral hepatitis. Patient medications included ferrous sulfate, Metamucil, and ibuprofen. Family history included atherosclerotic coronary artery disease in the father; pancreatic cancer in the mother; stress reaction in the sibling(s); and cerebrovascular disease, breast cancer, and uterine cancer in the grandparent(s). cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

The frozen tissue was homogenized and lysed using a Brinkmann Homogenizer Polytron PT-3000 (Brinkmann Instruments, Westbury, N.Y.) in guanidiniLm isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted twice with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Catalog #18248-013, Gibco/BRL). The cDNAs were fractionated on a Sepharose CL4B column (Catalog #275105-01, Pharmacia), and those cDNAs exceeding 400 bp were ligated into pSport 1. The plasmid pSport 1 was subsequently transformed into DH5a™ competent cells (Catalog #18258-012, Gibco/BRL).

II Isolation and Sequencing of cDNA Clones

Plasmid DNA was released from the cells and purified using the REAL Prep 96 Plasmid Kit (Catalog #26173, QIAGEN, Inc.). The recommended protocol was employed except for the following changes: 1) the bacteria were cultured in 1 ml of sterile Terrific Broth (Catalog #22711, Gibco/BRL™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences of the Sequence Listing or amino acid sequences deduced from them were used as query sequences against databases such as GenBaik, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc Nat. Acad. Sci. 90:5893–3) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against Gen-Bank functional protein databases, mammalian (mamp), vertebrate (vrtp) and eukaryote (eukp), for homology. The relevant database for a particular match were reported as a Glxxx±p (where xxx is pri, rod, etc and if present, p=peptide). Product score, the calculation of which is shown below, was used to determine the electronic stringency. For an exact match, product score was set at 70 with a conservative lower limit set at approximately 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) supra; Altschul, S. F. et al. (1990) supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding CAVIII occurs. Abundance and percent abundance are also reported. Abundance directly reflects the number of times a particular transcript is represented in a cDNA library, and percent abundance is abundance divided by the total number of sequences examined in the cDNA library.

V Extension of CAVIII Encoding Polynucleotides

The nucleic acid sequence of Incyte Clone 2059155 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primeis are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |

| | |
|---|---|
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi Of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-base hybridization analysis of human genomic DNA digested with one of the following endonlucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conc itions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the CAVIII-encoding sequence, or any part thereof, is used to decrease or inhibit expression of naturally occurring CAVIII. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of CAVIII, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the CAVIII-encoding transcript.

IX Expression of CAVIII

Expression of CAVIII is accomplished by subcloning the cDNAs into appropriate vectors and transforming the vectors into host cells. In this case, the cloning vector is also used to express CAVIII in *E. coli*. Upstream of the cloning site, this vector contains a promoter for β-galactosidase, followed by sequence containing the amino-terminal Met, and the subsequent seven residues of β-galactosidase.

Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of CAVIII into the bacterial growth media which can be used directly in the following assay for activity.

X Demonstration of CAVIII Activity

A fluorometric assay described by Shingles, et al. (1997, Anal. Biochem. 252(1): 190–197) uses the fluorescent pH indicator 8-hydroxypyrene-1,3,6-trisulfonate (pyranine) in combination with stopped-flow fluorometry to measure CAVIII activity. A pH 6.0 solution is mixed with a pH 8.0 solution and the initial rate of bicarbonate dehydration is measured. Addition of carbonic anhydrase to the pH 6.0 solution enables the measurement of the initial rate of activity at physiological temperatures with resolution times of 2 ms. Shingles et al. used this assay to resolve differences in activity and sensitivity to sulfonamides by comparing mammalian carbonic anhydrase isoforms. The fluorescent technique's sensitivity allows the determination of initial rates with a protein concentration as little as 65 ng/ml.

XI Production of CAVIII Specific Antibodies

CAVIII that is substantially purified using PAGE electrophoresis (Sambrook, supra), or other purification techniques, is used to immunize rabbits and to produce antibodies using standard protocols. The amino acid sequence deduced from SEQ ID NO 2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those rear the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring CAVIII Using Specific Antibodies

Naturally occurring or recombinant CAVIII is substantially purified by immunoaffinity chromatography using antibodies specific for CAVIII. An immunoaffinity column is constructed by covalently coupling CAVIII antibody to an activated chromatographic resin, such as CNBr-activated Sepharose (Pharmacia & Upjohn). After the coupling, the resin is blocked and washed according to the manufacturer's instructions.

Media containing CAVIII is passed over the immunoaffinity column, and the column is washed under conditions that allow the preferential absorbance of CAVIII (e.g., high ionic strength buffers in the presence of detergent). The column is eluted under conditions that disrupt antibody/CAVIII binding (eg, a buffer of pH 2–3 or a high concentration of a chaotrope, such as urea or thiocyanate ion), and CAVIII is collected.

XIII Identification of Molecules Which Interact with CAVIII

CAVIII or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled CAVIII, washed, and any wells with labeled CAVIII complex are assayed. Data obtained using different concentrations of CAVIII are used to calculate values for the number, affinity, and association of CAVIII with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 328 amino acids
        (B) TYPE: amino acid
        (C) STRANDEDNESS: single
        (D) TOPOLOGY: linear (vii) IMMEDIATE SOURCE:
        (A) LIBRARY: OVARNOT03
        (B) CLONE: 2059155

(xi) SEQUENCE DESCRIPTION: SEQ ID NO:1:

Met Gly Ala Ala Ala Arg Leu Ser Ala Pro Arg Ala Leu Val Leu Trp
 1               5                  10                  15
```

```
Ala Ala Leu Gly Ala Ala Ala His Ile Gly Pro Ala Pro Asp Pro Glu
            20                  25                  30

Asp Trp Trp Ser Tyr Lys Asp Asn Leu Gln Gly Asn Phe Val Pro Gly
        35                  40                  45

Pro Pro Phe Trp Gly Leu Val Asn Ala Ala Trp Ser Leu Cys Ala Val
    50                  55                  60

Gly Lys Arg Gln Ser Pro Val Asp Val Glu Leu Lys Arg Val Leu Tyr
65                  70                  75                  80

Asp Pro Phe Leu Pro Leu Arg Leu Ser Thr Gly Gly Glu Lys Leu
                85                  90                  95

Arg Gly Thr Leu Tyr Asn Thr Gly Arg His Val Ser Phe Leu Pro Ala
                100                 105                 110

Pro Arg Pro Val Val Asn Val Ser Gly Pro Leu Leu Tyr Ser His
        115                 120                 125

Arg Leu Ser Glu Leu Arg Leu Leu Phe Gly Ala Arg Asp Gly Ala Gly
        130                 135                 140

Ser Glu His Gln Ile Asn His Gln Gly Phe Ser Ala Glu Val Gln Leu
145                 150                 155                 160

Ile His Phe Asn Gln Glu Leu Tyr Gly Asn Phe Ser Ala Ala Ser Arg
                165                 170                 175

Gly Pro Asn Gly Leu Ala Ile Leu Ser Leu Phe Val Asn Val Ala Ser
                180                 185                 190

Thr Ser Asn Pro Phe Leu Ser Arg Leu Leu Asn Arg Asp Thr Ile Thr
            195                 200                 205

Arg Ile Ser Tyr Lys Asn Asp Ala Tyr Phe Leu Gln Asp Leu Ser Leu
        210                 215                 220

Glu Leu Leu Phe Pro Glu Ser Phe Gly Phe Ile Thr Tyr Gln Gly Ser
225                 230                 235                 240

Leu Ser Thr Pro Pro Cys Ser Glu Thr Val Thr Trp Ile Leu Ile Asp
                245                 250                 255

Arg Ala Leu Asn Ile Thr Ser Leu Gln Met His Ser Leu Arg Leu Leu
            260                 265                 270

Ser Gln Asn Pro Pro Ser Gln Ile Phe Gln Ser Leu Ser Gly Asn Ser
        275                 280                 285

Arg Pro Leu Gln Pro Leu Ala His Arg Ala Leu Arg Gly Asn Arg Asp
    290                 295                 300

Pro Arg His Pro Glu Arg Arg Cys Arg Gly Pro Asn Tyr Arg Leu His
305                 310                 315                 320

Val Asp Gly Val Pro His Gly Arg
                325
```

(2) INFORMATION FOR SEQ ID NO:2:

(i) SEQUENCE CHARACTERISTICS:
        (A) LENGTH: 1512 base pairs
        (B) TYPE: nucleic acid
        (C) STRANDEDNESS: single
        (D) TOPOLOGY: linear (vii) IMMEDIATE SOURCE:
        (A) LIBRARY: OVARNOT03
        (B) CLONE: 2059155

(xi) SEQUENCE DESCRIPTION: SEQ ID NO:2:

```
CTGGAAANGA GANANGNAGG ANGAGGAGGA GATGCGGGAT GGAGACCTGG AGTTAGGTGG      60

CTTGGGAGAG CTTAATGAAA AGAGAACGGA GAGGAGGTGT GGGTTAGGAA CCAAGAGGTA     120

GCCCTGGGGG CAGCAGAAGG CTGAGAGGAG TAGGAAGATC AGGAGCTAGA GGGAGACTGG     180
```

```
AGGGTTCCGG GAAAAGAGCA GAGGAAAGAG GAAAGACACA GAGAGACGGG AGAGAGAAGA      240

AGAGTGGGTT TGAAGGGCGG ATCTCAGTCC CTGGCTGCTT TGGCATTTGG GGAACTGGGA      300

CTCCCTGTGG GGAGGAGAGG AAAGCTGGAA GTCCTGGAGG ACAGGGTCC CAGAAGGAGG       360

GGACAGAGGA GCTGAGAGAG GGGGGCAGGG CGTTGGGCAG GGGTCCCTCG GAGGCCTCCT      420

GGGGATGGGG GCTGCAGCTC GTCTGAGCGC CCCTCGAGCG CTGGTACTCT GGGCTGCACT      480

GGGGGCAGCA GCTCACATCG GACCAGCACC TGACCCCGAG GACTGGTGGA GCTACAAGGA      540

TAATCTCCAG GGAAACTTCG TGCCAGGGCC TCCTTTCTGG GGCCTGGTGA ATGCAGCGTG      600

GAGTCTGTGT GCTGTGGGGA AGCGGCAGAG CCCCGTGGAT GTGGAGCTGA AGAGGGTTCT      660

TTATGACCCC TTTCTGCCCC CATTAAGGCT CAGCACTGGA GGAGAGAAGC TCCGGGGAAC      720

CTTGTACAAC ACCGGCCGAC ATGTCTCCTT CCTGCCTGCA CCCCGACCTG TGGTCAATGT      780

GTCTGGAGGT CCCCTCCTTT ACAGCCACCG ACTCAGTGAA CTGCGGCTGC TGTTTGGAGC      840

TCGCGACGGA GCCGGCTCGG AACATCAGAT CAACCACCAG GGCTTCTCTG CTGAGGTGCA      900

GCTCATTCAC TTCAACCAGG AACTCTACGG GAATTTCAGC GCTGCCTCCC GCGGCCCCAA      960

TGGCCTGGCC ATTCTCAGCC TCTTTGTCAA CGTTGCCAGT ACCTCTAACC CATTCCTCAG     1020

TCGCCTCCTT AACCGCGACA CCATCACTCG CATCTCCTAC AAGAATGATG CCTACTTTCT     1080

TCAAGACCTG AGCCTGGAGC TCCTGTTCCC TGAATCCTTC GGCTTCATCA CCTATCAGGG     1140

CTCTCTCAGC ACCCCGCCCT GCTCCGAGAC TGTCACCTGG ATCCTCATTG ACCGGGCCCT     1200

CAATATCACC TCCCTTCAGA TGCACTCCCT GAGACTCCTG AGCCAGAATC CTCCATCTCA     1260

GATCTTCCAG AGCCTCAGCG GTAACAGCCG GCCCCTGCAG CCCTTGGCCC ACAGGGCACT     1320

GAGGGGCAAC AGGGACCCCC GGCACCCCGA GAGGCGCTGC CGAGGCCCCA ACTACCGCCT     1380

GCATGTGGAT GGTGTCCCCC ATGGTCGCTG AGACTCCCCT TCGAGGATTG CACCCGCCCG     1440

TCCTAAGCCT CCCCACAAGG CGAGGGGAGT TACCCCTAAA ACAAAGCTAT TAAAGGGACA     1500

GAATACTTCC TG                                                        1512

(2) INFORMATION FOR SEQ ID NO:3:

(i) SEQUENCE CHARACTERISTICS:
        (A) LENGTH: 1345 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1532042

(xi) SEQUENCE DESCRIPTION: SEQ ID NO:3:

Cys Thr Cys Gly Ala Gly Cys Cys Thr Gly Gly Ala Gly Gly Thr
  1               5                  10                  15

Thr Cys Gly Gly Gly Ala Ala Ala Gly Gly Ala Ala Gly Gly Gly
                 20                  25                  30

Ala Ala Gly Gly Cys Ala Ala Gly Cys Gly Ala Gly Gly Gly Ala
                 35                  40                  45

Gly Ala Gly Gly Ala Gly Ala Gly Ala Gly Ala Gly Gly Ala Gly
                 50                  55                  60

Ala Gly Gly Gly Thr Gly Gly Gly Gly Thr Cys Cys Cys Ala
 65                  70                  75                  80

Gly Ala Thr Cys Cys Cys Gly Cys Thr Gly Cys Cys Thr Cys Gly
                 85                  90                  95
```

-continued

```
Thr Ala Ala Cys Thr Gly Gly Gly Gly Ala Ala Cys Thr Gly Gly Gly
            100                 105                 110

Ala Cys Thr Cys Cys Cys Thr Gly Cys Ala Gly Gly Ala Gly Gly Ala
        115                 120                 125

Gly Cys Gly Gly Ala Ala Gly Gly Cys Thr Gly Gly Ala Ala Gly Thr
    130                 135                 140

Cys Cys Thr Gly Gly Gly Ala Gly Gly Gly Ala Thr Thr Ala Gly Gly
145                 150                 155                 160

Gly Thr Thr Cys Cys Ala Cys Ala Ala Ala Gly Ala Gly Gly Gly Gly
                165                 170                 175

Gly Ala Gly Ala Ala Gly Cys Thr Gly Ala Gly Ala Gly Ala Gly Gly
            180                 185                 190

Gly Cys Cys Gly Gly Cys Cys Gly Gly Gly Ala Cys Ala Thr Thr Gly
        195                 200                 205

Gly Gly Ala Ala Gly Gly Gly Gly Thr Cys Ala Cys Cys Cys Cys Gly
    210                 215                 220

Ala Gly Gly Cys Cys Thr Cys Thr Thr Gly Gly Gly Gly Ala Thr Gly
225                 230                 235                 240

Gly Gly Gly Gly Cys Thr Gly Cys Ala Cys Cys Thr Cys Gly Thr Cys
                245                 250                 255

Thr Gly Ala Gly Cys Gly Cys Cys Cys Cys Thr Cys Gly Gly Gly Thr
            260                 265                 270

Gly Thr Thr Gly Gly Thr Ala Cys Thr Cys Thr Gly Gly Gly Cys Cys
        275                 280                 285

Gly Cys Ala Cys Thr Gly Gly Gly Ala Gly Cys Gly Gly Cys Ala Cys
    290                 295                 300

Gly Thr Cys Ala Cys Ala Thr Cys Gly Gly Ala Cys Cys Cys Gly Cys
305                 310                 315                 320

Ala Cys Cys Thr Gly Ala Cys Cys Ala Gly Ala Gly Gly Ala Cys Thr
                325                 330                 335

Gly Gly Thr Gly Gly Ala Gly Cys Thr Ala Cys Ala Gly Gly Gly Ala
            340                 345                 350

Thr Ala Ala Thr Cys Thr Cys Ala Gly Gly Gly Ala Ala Ala Cys Thr
        355                 360                 365

Thr Cys Gly Thr Gly Cys Cys Ala Gly Gly Ala Cys Cys Thr Cys Cys
    370                 375                 380

Cys Thr Thr Cys Thr Gly Gly Gly Gly Cys Cys Thr Gly Gly Thr Gly
385                 390                 395                 400

Ala Ala Cys Gly Cys Ala Gly Cys Cys Thr Gly Gly Ala Gly Thr Cys
                405                 410                 415

Thr Cys Thr Gly Thr Gly Cys Cys Gly Thr Gly Gly Gly Ala Ala Gly
            420                 425                 430

Cys Gly Thr Cys Ala Gly Ala Gly Cys Cys Cys Cys Gly Thr Gly Gly
        435                 440                 445

Ala Thr Gly Thr Gly Gly Ala Cys Gly Thr Gly Ala Ala Gly Ala Gly
    450                 455                 460

Gly Gly Thr Cys Cys Thr Cys Thr Ala Thr Gly Ala Cys Cys Cys Cys
465                 470                 475                 480

Thr Thr Cys Cys Thr Gly Cys Cys Cys Cys Cys Thr Cys Thr Gly Ala
                485                 490                 495

Gly Ala Cys Thr Cys Ala Gly Cys Ala Cys Cys Gly Gly Gly Gly Ala
            500                 505                 510

Gly Ala Gly Ala Ala Gly Cys Cys Thr Cys Cys Gly Thr Gly Gly Ala
        515                 520                 525

-continued

```
Ala Cys Thr Cys Thr Gly Thr Ala Cys Ala Ala Cys Ala Cys Gly
530                 535                 540
Gly Thr Cys Gly Cys Cys Ala Thr Gly Thr Cys Thr Cys Cys Thr
545                 550                 555                 560
Cys Cys Thr Gly Cys Cys Thr Gly Cys Gly Cys Cys Cys Gly Gly
                565                 570                 575
Cys Cys Thr Gly Thr Gly Gly Thr Ala Ala Thr Gly Thr Gly Thr
                580                 585                 590
Cys Thr Gly Gly Gly Gly Gly Ala Cys Cys Thr Cys Cys Thr
            595                 600                 605
Thr Thr Ala Thr Ala Gly Cys Cys Ala Cys Gly Ala Cys Thr Cys
610                 615                 620
Ala Gly Thr Gly Ala Ala Cys Thr Gly Cys Gly Gly Cys Thr Gly Cys
625                 630                 635                 640
Thr Ala Thr Thr Thr Gly Gly Gly Ala Gly Cys Ala Cys Gly Gly Ala
                645                 650                 655
Cys Gly Gly Ala Gly Cys Thr Gly Gly Cys Thr Cys Thr Gly Ala Ala
                660                 665                 670
Cys Ala Cys Cys Ala Gly Ala Thr Cys Ala Ala Cys Cys Ala Thr Cys
                675                 680                 685
Ala Gly Gly Thr Thr Thr Cys Thr Cys Thr Cys Thr Gly Ala
690                 695                 700
Gly Gly Thr Gly Cys Ala Ala Cys Thr Cys Ala Thr Cys Cys Ala Cys
705                 710                 715                 720
Thr Thr Cys Ala Ala Cys Cys Ala Ala Gly Ala Ala Cys Thr Cys Thr
                725                 730                 735
Ala Thr Gly Gly Gly Ala Ala Cys Cys Thr Cys Ala Gly Thr Gly Cys
                740                 745                 750
Cys Gly Cys Cys Ala Cys Ala Gly Gly Gly Cys Cys Cys
                755                 760                 765
Ala Ala Thr Gly Gly Cys Cys Thr Gly Gly Cys Cys Ala Thr Thr Cys
770                 775                 780
Thr Cys Ala Gly Cys Cys Thr Cys Thr Thr Thr Gly Thr Cys Ala Ala
785                 790                 795                 800
Thr Gly Thr Gly Gly Cys Thr Gly Gly Thr Ala Gly Cys Thr Cys Ala
                805                 810                 815
Ala Ala Cys Cys Cys Gly Thr Thr Cys Cys Thr Cys Ala Gly Ala Cys
                820                 825                 830
Gly Cys Cys Thr Cys Cys Thr Ala Ala Cys Cys Gly Thr Gly Ala
                835                 840                 845
Cys Ala Cys Cys Ala Thr Cys Ala Cys Cys Gly Cys Ala Thr Cys
                850                 855                 860
Thr Cys Cys Thr Ala Thr Ala Ala Gly Ala Ala Thr Gly Ala Thr Gly
865                 870                 875                 880
Cys Cys Thr Ala Cys Thr Thr Cys Thr Thr Cys Ala Ala Gly Ala
                885                 890                 895
Cys Cys Thr Gly Ala Gly Cys Cys Thr Gly Gly Ala Gly Cys Thr Cys
                900                 905                 910
Cys Thr Gly Thr Gly Cys Cys Cys Gly Ala Gly Thr Cys Cys Thr
                915                 920                 925
Thr Thr Gly Gly Cys Thr Thr Cys Ala Thr Cys Ala Cys Cys Thr Ala
                930                 935                 940
Thr Cys Ala Gly Gly Gly Cys Thr Cys Thr Cys Thr Cys Ala Gly Cys
```

-continued

```
                945                 950                 955                 960
Ala Cys Cys Cys Cys Ala Cys Cys Cys Thr Gly Thr Cys Gly Gly
                    965                 970                 975
Ala Gly Ala Cys Thr Gly Thr Thr Ala Cys Cys Thr Gly Gly Ala Thr
                    980                 985                 990
Cys Cys Thr Cys Ala Thr Thr Gly Ala Cys Ala Gly Gly Cys Cys
                    995                1000                1005
Cys Thr Cys Ala Ala Thr Ala Thr Cys Ala Cys Cys Thr Cys Cys
                   1010                1015                1020
Thr Cys Cys Ala Gly Cys Thr Gly Cys Ala Thr Thr Cys Cys Cys Thr
1025                1030                1035                1040
Gly Cys Gly Ala Cys Thr Thr Cys Thr Gly Ala Gly Cys Cys Ala Gly
                   1045                1050                1055
Ala Ala Thr Cys Cys Thr Cys Cys Gly Gly Gly Thr Cys Cys Ala
                   1060                1065                1070
Gly Thr Cys Thr Thr Cys Cys Ala Gly Ala Gly Cys Thr Cys Ala Gly
                   1075                1080                1085
Cys Cys Gly Thr Ala Ala Cys Gly Gly Cys Cys Gly Gly Cys Cys Cys
                   1090                1095                1100
Cys Thr Gly Cys Ala Gly Cys Cys Cys Thr Thr Cys Cys Gly Gly Cys
1105                1110                1115                1120
Ala Cys Ala Gly Gly Gly Cys Cys Thr Gly Ala Gly Gly Gly Gly
                   1125                1130                1135
Cys Ala Ala Cys Ala Gly Gly Ala Cys Cys Cys Cys Gly Gly Cys
                   1140                1145                1150
Cys Ala Cys Cys Cys Gly Ala Gly Ala Gly Gly Gly Thr Gly Cys
                   1155                1160                1165
Gly Gly Ala Gly Gly Gly Cys Cys Cys Ala Ala Cys Thr Ala Cys Cys
                   1170                1175                1180
Gly Cys Cys Thr Gly Cys Ala Thr Gly Thr Gly Gly Ala Thr Gly Ala
1185                1190                1195                1200
Thr Gly Thr Cys Cys Cys Cys Cys Ala Thr Gly Gly Thr Cys Thr Cys
                   1205                1210                1215
Thr Gly Ala Gly Ala Cys Thr Cys Cys Cys Ala Thr Cys Gly Ala
                   1220                1225                1230
Gly Gly Ala Gly Thr Cys Cys Gly Cys Cys Thr Gly Cys Cys Thr Thr
                   1235                1240                1245
Thr Cys Cys Cys Ala Ala Gly Cys Cys Thr Cys Cys Cys Ala Cys
                   1250                1255                1260
Cys Gly Ala Gly Gly Gly Gly Ala Gly Gly Gly Ala Gly Thr Gly
1265                1270                1275                1280
Cys Ala Cys Cys Cys Cys Ala Ala Ala Cys Ala Ala Gly
                   1285                1290                1295
Cys Thr Ala Thr Thr Ala Ala Ala Gly Gly Gly Ala Cys Ala Gly Ala
                   1300                1305                1310
Ala Thr Ala Cys Thr Thr Cys Cys Thr Gly Thr Ala Ala Ala Ala
                   1315                1320                1325
Ala Ala Ala Ala Ala Ala Ala Ala Ala Ala Ala Ala Ala
                   1330                1335                1340
Ala
1345
```

What is claimed is:

1. An isolated and purified polynucleotide sequence encoding a polypeptide comprising the amino acid sequence of SEQ ID NO:1.

2. A composition comprising the polynucleotide sequence of claim 1.

3. An isolated and purified polynucleotide sequence which is fully complementary to the polynucleotide sequence of claim 1.

4. An isolated and purified polynucleotide sequence comprising SEQ ID NO:2.

5. An isolated and purified polynucleotide sequence which is fully complementary to the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

9. A method for detecting a polynucleotide encoding CAVIII in a biological sample containing nucleic acids, the method comprising the steps of:

(a) hybridizing the polynucleotide of claim 3 to at least one of the nucleic acids of the biological sample, thereby forming a hybridization complex; and (b) detecting the hybridization complex, wherein the presence of the hybridization complex correlates with the presence of a polynucleotide encoding CAVIII in the biological sample.

10. The method of claim 9 wherein the nucleic acids of the biological sample are amplified by the polymerase chain reaction prior to the hybridizing step.

* * * * *